United States Patent [19]

Kellogg

[11] 4,432,970
[45] Feb. 21, 1984

[54] 6-BETA-HALOPENICILLANIC ACID 1,1-DIOXIDES AS BETA-LACTAMASE INHIBITORS

[75] Inventor: Michael S. Kellogg, Waterford, Conn.

[73] Assignee: Pfizer Inc., New York, N.Y.

[21] Appl. No.: 214,742

[22] Filed: Dec. 9, 1980

Related U.S. Application Data

[63] Continuation-in-part of Ser. No. 96,832, Nov. 23, 1979, Pat. No. 4,397,783.

[51] Int. Cl.$^3$ .................. C07D 499/00; A61K 31/425
[52] U.S. Cl. .............................. 424/114; 260/245.2 R; 424/270; 424/271
[58] Field of Search .............................. 424/114, 270; 260/245.2 R

[56] References Cited

U.S. PATENT DOCUMENTS

| | | | |
|---|---|---|---|
| 3,197,466 | 7/1965 | Chow et al. | 260/239.1 |
| 3,741,959 | 6/1973 | Looker et al. | 260/239.1 |
| 4,180,506 | 12/1979 | Pratt | 260/245.2 |
| 4,203,993 | 5/1980 | Gordon | 424/271 |
| 4,272,439 | 6/1981 | Ganguly et al. | 260/245.2 R |

FOREIGN PATENT DOCUMENTS 881675  8/1980  Belgium .
883390 11/1980  Belgium .
 13617  7/1980  European Pat. Off. .
2824535 12/1978  Fed. Rep. of Germany .
2044255 10/1980  United Kingdom .

OTHER PUBLICATIONS

Harrison et al., Journal of the Chemical Society (London), Perkin I, 1772 (1976).
Busson et al., "Recent Advances in the Chemistry of Beta-Lactam Antibiotics", J. Elks, ed., Burlington House, London, 1977, Chapter 32, pp. 304–313.
Clayton, Journal of the Chemical Society (London), Part C, 2123 (1969).
Daehne, Journal of Antibiotics, 33, 451, (1980).
Cartwright et al., Nature, 278, 360, (1979).

*Primary Examiner*—Nicholas S. Rizzo
*Attorney, Agent, or Firm*—Connolly and Hutz

[57] ABSTRACT

6-beta-Halopenicillanic acid 1,1-dioxides, physiologically acceptable salts thereof and esters thereof readily hydrolyzable; pharmaceutical compositions containing a 6-beta-halopenicillanic acid 1,1-dioxide, a physiologically acceptable salt thereof or an ester thereof readily hydrolyzable; and a method for enhancing the effectiveness of a beta-lactam antibiotic, using a 6-beta-halopenicillanic acid 1,1-dioxide, a physiologically acceptable salt thereof or an ester thereof readily hydrolyzable.

11 Claims, No Drawings

6-BETA-HALOPENICILLANIC ACID 1,1-DIOXIDES AS BETA-LACTAMASE INHIBITORS

CROSS REFERENCE TO RELATED APPLICATIONS

This application is a continuation-in-part of application Ser. No. 096,832 filed Nov. 23, 1979 now 4,397,783, which in turn is a continuation-in-part of application Ser. No. 17,809 filed Mar. 5, 1979, and now abandoned.

BACKGROUND OF THE INVENTION

One of the most well-known and widely-used classes of antibacterial agents in the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin, amoxicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components.

Thus, according to the invention, there are provided certain new chemcial compounds which are inhibitors of microbial, especially bacterial, beta-lactamases. More specifically, these new chemical compounds are 6-beta-halopenicillanic acid 1,1-dioxides, pharmaceutically-acceptable base salts thereof, i.e. physiologically acceptable salts thereof, and readily hydrolyzable esters thereof. Of the aforesaid esters, those which are readily hydrolyzable in vivo are of course preferred. Additionally, there is provided a method for enhancing the effectiveness of beta-lactam antibiotics using said new chemical compounds, and pharmaceutical compositions comprising said new chemical compounds.

U.S. Pat. No. 4,234,579 discloses the use of penicillanic acid 1,1-dioxide, and esters thereof readily hydrolyzable in vivo, as antibacterial agents and as beta-lactamase inhibitors. U.S. Pat. No. 4,180,506 discloses 6-beta-bromopenicillanic acid as an antibacterial agent and as a beta-lactamase inhibitor.

Harrison et al., *Journal of the Chemical Society* (London), Perkin I, 1772 (1976) disclose: (a) the oxidation of 6,6-dibromopenicillanic acid with 3-chloroperbenzoic acid, to give a mixture of the corresponding alpha- and beta-sulfoxides; (b) oxidation of methyl 6,6-dibromopenicillanate with 3-chloroperbenzoic acid to give a methyl 6,6-dibromopenicillanate 1,1-dioxide; (c) oxidation of methyl 6-alpha-chloropenicillanate with 3-chloroperbenzoic acid, to give a mixture of the corresponding alpha- and beta-sulfoxides; and (d) oxidation of methyl 6-alpha-bromopenicillanate with 3-chloroperbenzoic acid, to give a mixture of the corresponding alpha- and beta-sulfoxides.

Clayton, *Journal of the Chemical Society* (London), Part C, 2123 (1969) discloses inter alia: (a) 6-alpha-iodopenicillanic acid and its methyl ester; and (b) 6,6-diiodopenicillanic acid and its methyl ester.

SUMMARY OF THE INVENTION

According to the invention, there are provided penicillanic acid derivatives of the formula I:

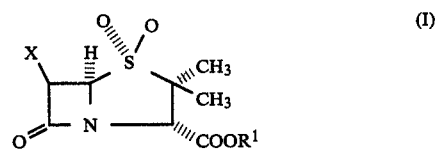

and the pharmaceutically-acceptable base salts thereof, wherein $R^1$ is hydrogen or a readily hydrolyzable ester-forming residue, especially an ester-forming residue readily hydrolyzable in vivo; and X is chloro, bromo or iodo. Said compounds of formula I are useful as beta-lactamase inhibitors, and they increase the effectiveness of several beta-lactam antibiotics against many beta-lactamase producing microorganisms.

Also, according to the invention, there are provided pharmaceutical compositions which comprise a compound of formula I, or a pharmaceutically-acceptable base salt thereof, and a pharmaceutically-acceptable carrier.

Also, according to the invention there is provided a method of increasing the effectiveness of a beta-lactam antibiotic in a mammalian, particularly human, subject, which comprises co-administering, with said beta-lactam antibiotic, to said human subject, a beta-lactam antibiotic effectiveness increasing amount of a compound of formula I, or a pharmaceutically acceptable base salt thereof.

A preferred group of compounds of formula I is the group in which X is bromo. An especially preferred individual compound of the invention is 6-beta-bromopenicillanic acid 1,1-dioxide, the compound of formula I, wherein $R^1$ is hydrogen and X is bromo. This latter compound can also be named as (2S,5R,6R)-6-beta-bromo-3,3-dimethyl-7-oxo-4-thia-1-azabicyclo[3.2.0]heptane-2-carboxylic acid, S,S-dioxide. The physiologically acceptable salts and the readily hydrolyzable esters of this latter compound are also preferred compounds.

6-alpha-Halopenicillanic acid 1,1-dioxides, and esters thereof readily hydrolyzable in vivo, are being claimed in application Ser. No. 214,757 filed Dec. 9, 1980. A process for preparing penicillanic acid 1,1-dioxide, and esters thereof readily hydrolyzable in vivo, which uses as intermediates both 6-alpha- and 6-beta-halo-penicillanic acid 1,1-dioxides, and esters thereof readily hydrolyzable in vivo, is being claimed in application Ser. No. 214,756 filed Dec. 9, 1980.

DETAILED DESCRIPTION OF THE INVENTION

This invention relates to compounds of the formula I, and to several intermediates therefor. Throughout this specification, these compounds are named as derivatives of penicillanic acid, which is represented by the following structural formula:

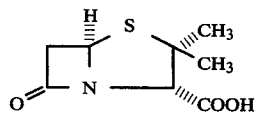
(II)

In derivatives of penicillanic acid, broken line attachment of a substituent to the bicyclic nucleus indicates that the substituent is below the plane of the nucleus. Such a substituent is said to be in the alpha-configuration. Conversely, solid line attachment of a substituent to the bicyclic nucleus indicates that the substituent is above the plane of the nucleus. This latter configuration is referred to as the beta-configuration. Thus, the group X has the beta-configuration in formula I.

In this specification, where $R^1$ is an ester-forming residue readily hydrolyzable in vivo, it is a grouping which is notionally derived from an alcohol of the formula $R^1$—OH, such that the moiety $COOR^1$ in such a compound of formula I represents an ester grouping. Moreover, $R^1$ is of such a nature that the grouping $COOR^1$ is readily cleaved in vivo to liberate a free carboxy group (COOH). That is to say, $R^1$ is a group of the type that when a compound of formula I, wherein $R^1$ is an ester-forming residue readily hydrolyzed in vivo, is exposed to mammalian blood or tissue, the compound of formula I, wherein $R^1$ is hydrogen, is readily produced. The groups $R^1$ are well known in the penicillin art. In most instances, they improve the absorption characteristics of the penicillin compound. Additionally, $R^1$ should be of such a nature that it imparts pharmaceutically-acceptable properties to a compound of formula I, and it liberates pharmaceutically-acceptable fragments when cleaved in vivo. The groups $R^1$ are well known and are readily identified by those skilled in the penicillin art. See, for example, West German Offenlegungsschrift No. 2,517,316. Specific examples of groups for $R^1$ are 3-phthalidyl, 4-crotonolactonyl, gamma-butyrolacton-4-yl and groups of the formula

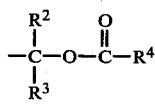
III and

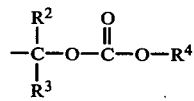
IV wherein $R^2$ and $R^3$ are each selected from the group consisting of hydrogen and alkyl having from 1 to 2 carbon atoms, and $R^4$ is alkyl having from 1 to 5 carbon atoms. However, preferred groups for $R^1$ are alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

3-Phthalidyl, 4-crotonolactonyl and gamma-butyrolacton-4-yl refer to structures V, VI and VII. The wavy lines are intended to denote either of the two epimers or a mixture thereof.

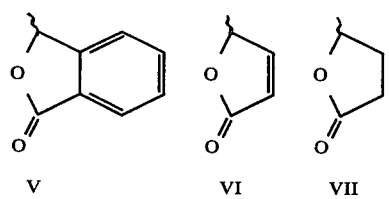

V   VI   VII

The compounds of formula I can be prepared by oxidation of the sulfide group in a compound of the formula:

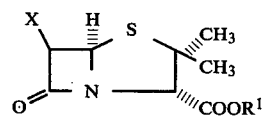
(VIII)

wherein $R^1$ and X are as defined previously, to give the sulfone grouping.

A wide variety of oxidants known in the art for the oxidation of sulfides to sulfones can be used for this process. However, particularly convenient reagents are alkali metal permanganates such as sodium and potassium permanganate; alkaline earth metal permanganates, such as calcium and barium permanganates; and organic peroxycarboxylic acids, such as peracetic acid and 3-chloroperbenzoic acid.

When a compound of the formula VIII, wherein $R^1$ and X are as defined previously, is oxidized to the corresponding compound of the formula I using a metal permanganate, the reaction is usually carried out by treating the compound of the formula VIII with from about 1 to about five molar equivalents, and preferably about two molar equivalents, of the permanganate in an appropriate, reaction-inert solvent system. An appropriate, reaction-inert solvent system is one that does not adversely interact with either the starting materials or the product, and water is commonly used. If desired, a co-solvent which is miscible with water but will not interact with the permanganate, such as tetrahydrofuran, can be added. The reaction can be carried out at a temperature in the range from about −20° to about 50° C., and it is preferably carried out at about 0° C. At about 0° C. the reaction is normally substantially complete within a short period, e.g. within one hour. Although the reaction can be carried out under neutral, basic or acid conditions, it is preferable to operate under substantially neutral conditions in order to avoid decomposition of the beta-lactam ring system of the compounds of the formulae I and VIII. Indeed, it is often advantageous to buffer the pH of the reaction medium in the vicinity of neutrality. The sulfone is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula VIII, wherein X and $R^1$ are as previously defined, is oxidized to the corresponding compound of the formula I using a peroxycarboxylic acid, the reaction is usually carried out by treating the compound of the formula VIII with from about 2 to about 4 molar equivalents, and preferably about 2.2 molar equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about $-20°$ to about $50°$ C., and preferably at about $0°$ C. At about $25°$ C., reaction times of about 2 to about 16 hours are commonly used. The product is normally isolated by removal of the solvent by evaporation in vacuo. The product can be purified by conventional methods, well known in the art.

When it is desired to prepare a compound of formula I, wherein $R^1$ is hydrogen, from a compound of formula VIII, wherein $R^1$ is hydrogen, it is possible to block the free carboxy group first with a conventional penicillin carboxy protecting group. The sulfide moiety is then oxidized, and finally the carboxy protecting group is removed with regeneration of the free carboxy group. In this regard, a variety of protecting groups conventionally used in the penicillin art to protect the 3-carboxy group can be employed. The identity of the protecting group is not critical. The major requirements for the protecting group are that it must be stable during the oxidation step, and it must be removable from the particular compound of formula I, using conditions under which the beta-lactam ring system remains substantially intact. Typical examples are the tetrahydropyranyl group, trialkylsilyl groups, the benzyl group, substituted benzyl groups (e.g. 4-nitrobenzyl), the benzhydryl group, the 2,2,2-trichloroethyl group, the t-buty group and the phenacyl group. Although all protecting groups are not operable in all situations, a particular group which can be used in a particular situation will be readily selected by one skilled in the art. See further: U.S. Pat. Nos. 3,632,850 and 3,197,466; British Pat. No. 1,041,985, Woodward et al, *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporin and Penicillins, Chemistry and Biology", edited by H. E. Flynn, Academic Press, Inc., 1972. The penicillin carboxy protecting group is removed in conventional manner, having due regard for the lability of the beta-lactam ring system.

The compounds of formula I, wherein $R^1$ is an ester-forming residue readily hydrolyzable in vivo can be prepared directly from the corresponding compound of formula I wherein $R^1$ is hydrogen, by esterification. The specific method chosen will depend naturally upon the precise structure of the ester-forming residue, but an appropriate method will be readily selected by one skilled in the art. In the case wherein $R^1$ is selected from the group consisting of 3-phthalidyl, 4-crotonolactonyl, gamma-butyrolacton-4-yl and groups of the formula III and IV, wherein $R^2$, $R^3$ and $R^4$ are as defined previously, they can be prepared by alkylation of the appropriate compound of formula I, wherein $R^1$ is hydrogen, with a 3-phthalidyl halide, a 4-crotonolactonyl halide, a gamma-butyrolacton-4-yl halide or a compound of the formula

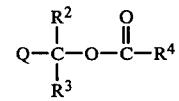

and

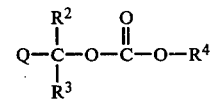

wherein Q is halo, and $R^2$, $R^3$ and $R^4$ are as previously defined. The terms "halide" and "halo" are intended to mean derivatives of chlorine, bromine and iodine. The reaction is conveniently carried out by dissolving a salt of said compound of formula I, wherein $R^1$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salts, and tertiary amine salts, such as triethylamine, ethyldiisopropylamine, N-ethylpiperidine, N,N-dimethyl-aniline and N-methylmorpholine salts. The reaction is run at a temperature in the range from about $0°$ to $100°$ C., and usually at about $25°$ C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

6-beta-Chloropenicillanic acid 1,1-dioxide (or a readily hydrolyzable ester thereof) can be prepared by reduction of 6-chloro-6-iodopenicillanic acid 1,1-dioxide (or a readily hydrolyzable ester thereof) using tri-n-butyltin hydride, tribenzyltin hydride, diphenylbenzyltin hydride, dibenzylphenyltin hydride or triphenyltin hydride; 6-beta-bromopenicillanic acid 1,1-dioxide (or a readily hydrolyzable ester thereof) can be prepared by reduction of 6,6-dibromopenicillanic acid 1,1-dioxide (or a readily hydrolyzable ester thereof) using tri-n-butyltin hydride, tribenzyltin hydride, diphenylbenzyltin hydride, dibenzylphenyltin hydride or triphenyltin hydride; and 6-beta-iodopenicillanic acid 1,1-dioxide can be prepared by reduction of 6,6-diiodopenicillanic acid 1,1-dioxide (or a readily hydrolyzable ester thereof) by reduction with tri-n-butyltin hydride, tribenzyltin hydride, diphenylbenzyltin hydride, dibenzylphenyltin hydride or triphenyltin hydride. The 6-chloro-6-iodo-, 6,6-dibromo- and 6,6-diiodopenicillanic acid 1,1-dioxides (or a readily hydrolyzable ester thereof) can be prepared from the corresponding sulfide by oxidation with a metal permanganate or a peroxycarboxylic acid, using methods previously described.

Included within the scope of this invention are the pharmaceutically-acceptable base salts, which can also be termed physiologically acceptable salts, of the compounds of formula I, wherein $R^1$ is hydrogen. Said pharmaceutically-acceptable base salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Pharmaceutically-acceptable base salts which are especially useful are metal salts, e.g. alkali metal or alkaline earth metal salts, and amine salts. Representative examples are sodium, potassium, calcium, ethanolamine, diethanolamine, ethylenediamine, piperazine, procaine and glycine salts. Especially preferred salts are sodium and potassium salts. Basic agents which are suitably employed in salt formation belong to both the organic and inorganic types, and they include organic amines, alkali metal hydroxides, carbonates, bicarbonates, hydrides and alkoxides, as well as alkaline earth metal hydroxides, carbonates, hydrides and alkoxides, and also alkali metal salts of long-chain fatty acids, e.g. sodium 2-ethylhexanoate.

6-beta-Chloropenicillanic acid, 6-beta-bromopenicillanic acid and 6-beta-iodopenicillanic acid are prepared by reduction of 6-chloro-6-iodopenicillanic acid, 6,6-dibromopenicillanic acid and 6,6-diiodopenicillanic acid, respectively, with tri-n-butyltin hydride or triphenyltin hydride. 6-Chloro-6-iodopenicillanic acid is prepared by diazotization of 6-aminopenicillanic acid in the presence of iodine chloride; 6,6-dibromopenicillanic acid is prepared by the method of Clayton, *Journal of the Chemical Society* (London) (C) 2123 (1969); and 6,6-diiodopenicillanic acid is prepared by diazotization of 6-aminopenicillanic acid in the presence of iodine.

6-beta-Iodopenicillanic acid also can be prepared from 6-alpha-trifluoromethylsulfonyloxypenicillanic acid by treatment with a metal iodide such as sodium iodide. 6-alpha-Trifluoromethylsulfonyloxypenicillanic acid can be contained by diazotization of the benzhydryl or 4-methoxybenzyl ester of 6-beta-aminopenicillanic acid, followed by treatment with trifluoromethanesulfonic acid, to give benzhydryl or 4-methoxybenzyl 6-alpha-trifluoromethylsulfonyloxypenicillanate, followed in turn by removal of the ester protecting group using trifluoroacetic acid. Alternatively, 6-beta-iodopenicillanic acid can be obtained from benzhydryl or 4-methoxybenzyl 6-alpha-trifluoromethylsulfonyloxypenicillanate by reaction with a metal iodide, such as sodium iodide, followed by removal of the ester protecting group using trifluoroacetic acid. Also benzylhydryl or 4-methoxybenzyl 6-alpha-trifluoromethylsulfonyloxypenicillanate can be prepared from the 6-alpha hydroxy compound by acylation using trifluoromethanesulfonyl chloride.

The compounds of formula I, wherein $R^1$ is hydrogen are inhibitors of bacterial beta-lactamases in vitro and in vivo, and they will increase the antibacterial effectiveness of many beta-lactam antibiotics (penicillins and cephalosporins) against many microorganisms which produce a beta-lactamase, both in vitro and in vivo. The compounds of formula I, wherein $R^1$ is an ester-forming residue readily hydrolyzable in vivo are inhibitors of bacterial beta-lactamases in vivo, and they will increase the antibacterial effectiveness of many beta-lactam antibiotics (penicillins and cephalosporins) against many microorganisms which produce a beta-lactamase, in vivo. The manner in which the compounds of the formula I, wherein $R^1$ is hydrogen, increase the effectiveness of a beta-lactam antibiotic in vitro can be appreciated by reference to experiments in which the MIC (Minimum Inhibitory Concentration) of a given antibiotic alone, and a compound of the formula I alone, are measured. These MIC's are then compared with the MIC values obtained with a combination of the given antibiotic and the compound of the formula I. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of formula I enhance the antibacterial effectiveness of beta-lactam antibiotics in vivo. That is, they lower the amount of the antibiotic which is needed to protect mice against an otherwise lethal inoculum of certain beta-lactamase producing bacteria.

The ability of the compounds of formula I to enhance the effectiveness of a beta-lactam antibiotic against beta-lactamase-producing bacteria makes they valuable for co-administration with beta-lactam antibiotics in the treatment of bacterial infections in mammals, particularly man. In the treatment of a bacterial infection, the compound of the formula I can be comingled with the beta-lactam antibiotic, and the two agents thereby administered simultaneously. Alternatively, the compound of the formula I can be administered as a separate agent during a course of treatment with a beta-lactam antibiotic. In some instances it will be advantageous to pre-dose the subject with the compound of the formula I before initiating treatment with a beta-lactam antibiotic.

When using a compound of formula I to enhance the effectiveness of a beta-lactam antibiotic, it is administered preferably in formulation with standard pharmaceutical carriers or diluents. A pharmaceutical composition comprising a pharmaceutically-acceptable carrier, a beta-lactam antibiotic and a compound of formula I will normally contain from about 5 to about 80 percent of the pharmaceutically acceptable carrier by weight.

When using the compounds of formula I in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula I and the beta-lactam antibiotic will normally be in the range from about 1:3 to 3:1. Additionally, when using the compounds of formula I in combination with another beta-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some case it may be necessary to use dosages outside these limits.

Typical beta-lactam antibiotics with which the compounds of formula I and their esters readily hydrolyzable in vivo can be co-administered are:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid
6-(D-2-amino-2-[4-hydroxyphenyl]acetamido)penicillanic acid,
6-(D-2-amino-2-[1,4-cyclohexadienyl]acetamido penicillanic acid;
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(D-2-amino-2-p-hydroxphenylacetamido)desacetoxycephalosporanic acid,
7-(2-[4-pyridylthio]acetamido)cephalosporanic acid,
7-(D-2-amino-2-[1,4-cyclohexadienyl]acetamido)cephalosporanic acid,
7-(D-2-amino-2-phenylacetamido)cephalosporanic acid,
7-[D-(−)-alpha-(4-ethyl-2,3,-dioxo-1-piperazinecarboxamido)-alpha-(4-hydroxyphenyl)acetamido]-3-[(1-methyl-1,2-3,4-tetrazol-5-yl)thiomethyl]-3-cephem-4-carboxylic acid,
7-(D-2-amino-2-phenylacetamido)-3-chloro-3-cephem-4-carboxylic acid,
7-[2-(2-amino-4-thiazolyl)-2-(methoximino)acetamido)-cephalosporanic acid,
[6R,7R-3-carbamoyloxymethyl-7(2Z)-2-methoxyimino(fur-2-yl)acetamido-ceph-3-em-4-carboxylate]
7-[2-(2-aminothiazol-4-yl)acetamido]-3-[((1-2-dimethylaminoethyl)-1H-tetrazol-5-yl]thio)methyl]ceph-3-em-4-carboxylic acid, and a pharmaceutically acceptable salt thereof.

Preferred beta-lactam antibiotics with which a compound of formula I or salt or ester thereof readily hydrolyzable in vivo can be co-administered are:
6-(2-phenylacetamido)penicillanic acid,
6-(2-phenoxyacetamido)penicillanic acid,
6-(D-2-amino-2-phenylacetamido)penicillanic acid,
6-(D-2-amino-2-[4-hydroxyphenyl]acetamido)penicillanic acid,
6-(2-carboxy-2-phenylacetamido)penicillanic acid
and the pharmaceutically acceptable salts thereof.

As will be appreciated by one skilled in the art, some of the above beta-lactam compounds are effective when administered orally or parenterally, while others are effective only when administered by the parenteral route. When a compound of formula I is to be used simultaneously (i.e. co-mingled) with a beta-lactam antibiotic which is effective only on parenteral administration, a combination formulation suitable for parenteral use will be required. When a compound of formula I is to be used simultaneously (co-mingled) with a beta-lactam antibiotic which is effective orally or parenterally, combinations suitable for either oral or parenteral administration can be prepared. Additionally, it is possible to administer preparations of a compound of formula I, while at the same time administering a further beta-lactam antibiotic parenterally; and it is also possible to administer preparations of a compound of formula I parenterally, while at the same time administering the further beta-lactam antibiotic orally.

The following examples are provided solely for the purpose of further illustration. Nuclear magnetic resonance spectra (NMR) were measured at 60 MHz for solutions in deuterochloroform (CDCl$_3$), perdeuterodimethyl sulfoxide (DMSO-d$_6$) or deuterium oxide (D$_2$O) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; bs, broad singlet; d, doublet; t, triplet; q, quartet; m, multiplet.

EXAMPLE 1

6-beta-Chloropenicillanic Acid 1,1-Dioxide

An oxidizing solution was prepared from 185 mg of potassium permanganate, 0.063 ml of 85% phosphoric acid and 5 ml of water. This oxidizing solution was added dropwise to a solution of 150 mg of sodium 6-beta-chloropenicillanate in 5 ml of water at 0°–5° C., until the purple color of the potassium permanganate persisted. Approximately half of the oxidizing solution was required. At this point, the potassium permanganate color was discharged by the addition of solid sodium bisulfite, and then the reaction mixture was filtered. Ethyl acetate was added to the filtrate and the pH was adjusted to 1.8. The layers were separated and the aqueous layer was further extracted with ethyl acetate. The combined ethyl acetate layers were washed with water, dried and evaporated in vacuo to give 118 mg of the title compound. The NMR spectrum (in CD$_3$COCD$_3$) showed absorption at 5.82 (d, 1H), 5.24 (d, 1H), 4.53 (s, 1H), 1.62 (s, 3H) and 1.50 (s, 3H) ppm.

The above product was dissolved in tetrahydrofuran and an equal volume of water was added. The pH was adjusted to 6.8 using dilute sodium hydroxide, the tetrahydrofuran was removed by evaporation in vacuo, and the residual aqueous solution was freezed dried. This afforded the sodium salt of the title compound.

EXAMPLE 2

6-beta-Bromopenicillanic Acid 1,1-Dioxide

To a solution of 255 mg of sodium 6-beta-bromopenicillanate in 5 ml of water, at 0° to 5° C., was added a solution prepared from 140 mg of potassium permanganate, 0.11 ml of 85% phosphoric acid and 5 ml of water, at 0° to 5° C. The pH was maintained between 6.0 and 6.4 during the addition. The reaction mixture was stirred at pH 6.3 for 15 minutes, and then the purple solution was covered with ethyl acetate. The pH was adjusted to 1.5 and 330 mg of sodium bisulfite was added. The pH was adjusted to 1.7 and stirring was continued. After 5 minutes, the layers were separated and the aqueous layer was further extracted with ethyl acetate. The combined ethyl acetate solutions were washed with brine, dried (MgSO$_4$) and evaporated in vacuo. This afforded 216 mg of the title compound as white crystals. The NMR spectrum (in D$_2$O) showed absorptions at 5.78 (d, 1H, J=4 Hz), 5.25 (d, 1H, J=4 Hz), 4.20 (s, 1H), 1.65 (s, 3H) and 1.46 (s, 3H) ppm. The IR spectrum (KBr disc) showed an absorption at 1790 cm$^{-1}$.

The latter product was suspended in ethyl acetate, and then a small volume of water, followed by 57 mg of sodium bicarbonate, was added. This mixture was stirred for 15 minutes, and then the aqueous phase was removed and lyophilized. This afforded 140 mg of the sodium salt of the title compound. The NMR spectrum (in D$_2$O) showed absorptions at 5.80 (d, J=4 Hz, 1H), 5.25 (d, J=4 Hz, 1H), 4.30 (s, 1H), 1.55 (s, 3H) and 1.45 (s, 3H). The IR spectrum (KBr disc) showed an absorption at 1790 cm$^{-1}$.

EXAMPLE 3

6-beta-Iodopenicillanic Acid 1,1-Dioxide

Oxidation of 6-beta-iodopenicillanic acid with potassium permanganate, according to the procedure of Example 4, affords 6-beta-iodopenicillanic acid, 1,1-dioxide.

EXAMPLE 4

Pivaloyloxymethyl 6-beta-Bromopenicillanate 1,1-Dioxide

To a solution of 394 mg of pivaloyloxymethyl 6-beta-bromopenicillanate in 10 ml of dichloromethane is added 400 mg of 3-chloroperbenzoic acid at 0° to 5° C. The reaction mixture is stirred at 0° to 5° C. for 1 hour and then at 25° C. hours. The filtered reaction mixture is evaporated to dryness in vacuo to give the title compound.

EXAMPLE 5

The procedure of Example 4 is repeated, except that the pivaloyloxymethyl 6-beta-bromopenicillanate is replaced by:
3-phthalidyl 6-beta-chloropenicillanate,
4-crotonolactonyl 6-beta-chloropenicillanate,
gamma-butyrolacton-4-yl 6-beta-bromopenicillanate,
acetoxymethyl 6-beta-bromopenicillanate,
pivaloyloxymethyl 6-beta-bromopenicillanate,
hexanoyloxymethyl 6-beta-iodopenicillanate,
1-(acetoxy)ethyl 6-beta-iodopenicillanate,
1-(isobutyryloxy)ethyl 6-beta-chloropenicillanate,
1-methyl-1-(acetoxy)ethyl 6-beta-chloropenicillanate,
1-methyl-1-(hexanoyloxy)ethyl 6-beta-bromopenicillanate,
methoxycarbonyloxymethyl 6-beta-bromopenicillanate,
propoxycarbonyloxymethyl 6-beta-bromopenicillanate,
1-(ethoxycarbonyloxy)ethyl 6-beta-bromopenicillanate,
1-butoxycarbonyloxy)ethyl 6-beta-iodopenicillanate,
1-methyl-1-(methoxycarbonyloxy)ethyl 6-beta-iodopenicillanate and
1-methyl-1-(isopropoxycarbonyloxy)ethyl 6-beta-chloropenicillanate,
respectively. This affords:
3-phthalidyl 6-beta-chloropenicillanate 1,1-dioxide,
4-crotonolactonyl 6-beta-chloropenicillanate 1,1-dioxide,
gamma-butyrolacton-4-yl 6-beta-bromopenicillanate 1,1-dioxide,
acetoxymethyl 6-beta-bromopenicillanate 1,1-dioxide,
pivaloyloxymethyl 6-beta-bromopenicillanate 1,1-dioxide,
hexanoyloxymethyl 6-beta-iodopenicillanate 1,1-dioxide,
1-(acetoxy)ethyl 6-beta-iodopenicillanate 1,1-dioxide,
1-(isobutyryloxy)ethyl 6-beta-chloropenicillanate 1,1-dioxide,
1-methyl-1-(acetoxy)ethyl 6-beta-chloropenicillanate 1,1-dioxide,
1-methyl-1-(hexanoyloxy)ethyl 6-beta-bromopenicillanate 1,1-dioxide,
methoxycarbonyloxymethyl 6-beta-bromopenicillanate 1,1-dioxide,
propoxycarbonyloxymethyl 6-beta-bromopenicillanate 1,1-dioxide, 1-(ethoxycarbonyloxy)ethyl 6-beta-bromopenicillanate 1,1-dioxide, 1-(butoxycarbonyloxy)ethyl 6-beta-iodopenicillanate 1,1-dioxide, 1-methyl-1-(methoxycarbonyloxy)ethyl 6-beta-iodopenicillanate 1,1-dioxide and 1-methyl-1-(isopropoxycarbonyloxy)ethyl 6-beta-chloropenicillanate 1,1-dioxide, respectively.

EXAMPLE 6

6-β-Chloropenicillanic Acid 1,1-Dioxide

6-chloro-6-iodopenicillanic 1,1-dioxide

To a suspension of 3.0 g. of 6-chloro-6-iodopenicillanic acid in a mixture of 25 ml. of methylene chloride and 15 ml. of water was added sufficient 3 N sodium hydroxide solution to give a pH of 7.0. The aqueous phase was separated and the organic layer extracted several times with water. The aqueous phase and the washings were combined, cooled to 5° C., and treated dropwise over a period of 20 min. with a solution comprised of 1.64 g. of potassium permanganate and 0.8 ml. of phosphoric acid in 25 ml. of water. The temperature was maintained at 5°–8° C. and the pH at 5.5–6.0 by the addition of 3 N sodium hydroxide solution.

Ethyl acetate (30 ml.) was added to the reaction and the pH adjusted to 1.5 with 6 N hydrochloric acid. A 10% solution of sodium bisulfite (20 ml.) was added dropwise, the pH being kept below 1.6 with 6 N hydrochloric acid. The layers were separated and the aqueous further extracted with ethyl acetate. The combined ethyl acetate layer and washings were dried over sodium sulfate and concentrated in vacuo to give 2.4 g. of the desired intermediate, m.p. 137°–139° C.

6-β-chloropenicillanic acid 1,1-dioxide

To a solution of 3.02 g. of 6-chloro-6-iodopenicillanic acid 1,1-dioxide in 125 ml. of toluene at 0°–5° C. is added, under a nitrogen atmosphere, 1.08 ml. of triethylamine followed by 0.977 ml. of trimethylsilyl chloride. After stirring 5 min. at 0°–5° C., 60 min. at 25° C. and 30 min. at 50° C., the reaction is cooled to 25° C. and the triethylamine hydrochloride removed by filtration. To the resulting filtrate is added 15 mg. of azobisisobutyronitrile, followed by 2.02 ml. of tribenzyltin hydride. The mixture is irradiated with ultraviolet light for 15 min. with external cooling to maintain the temperature at about 20°–25° C. The solvent is removed in vacuo and the residue dissolved in a 1:1 mixture of tetrahydrofuran-water. The pH is adjusted to 7.0 and the tetrahydrofuran removed under reduced pressure. The residual aqueous solution is extracted with diethyl ether followed by the addition of an equal volume of ethyl acetate. The pH is adjusted to 1.8 with 6 N hydrochloric acid and the organic phase separated. The aqueous is further extracted with ethyl acetate and the combined organic layer and washings are concentrated under vacuum to dryness to give the desired product.

EXAMPLE 7

6-β-Bromopenicillanic Acid Pivaloyloxymethyl Ester 1,1-Dioxide

6,6-dibromopenicillanic acid pivaloyloxymethyl ester 1,1-dioxide

To a solution of 1.8 g. of 6,6-dibromopenicillanic acid pivaloyloxymethyl ester in 50 ml. of chloroform was added 1.63 g. of 80% m-chloroperbenzoic acid, and the resulting reaction mixture allowed to stir at room temperature overnight. Water (30 ml.) was added to the reaction and sufficient sodium bisulfite was added to give a negative starch-iodine paper test. The pH was adjusted to 7.5 with dilute sodium hydroxide solution and the organic phase separated. The aqueous was further extracted with chloroform and the organic phase and washings were combined, dried over sodium sulfate and concentrated to dryness. The residue was chromatographed on 250 g. of silica gel using chloroform as the eluent. The fractions containing the product were combined and concentrated to give 1.2 g. of the desired compound.

6-β-bromopenicillanic acid pivaloyloxymethyl ester 1,1-dioxide

To a solution of 1.15 g. of 6,6-dibromopenicillanic acid pivaloyloxymethyl ester 1,1-dioxide in 10 ml. of toluene under a nitrogen atmosphere is added 500 mg. of triphenyltin hydride and a few crystals of azobisisobutyronitrile. The resulting reaction mixture is warmed to 40° C. for 30 min. An additional 250 mg. of hydride and small amounts of nitrile are added and the heating continued for an additional 30 min. The solvent is removed in vacuo and the residue treated with 150 ml. of chloroform. The mixture is filtered and the filtrate chromatographed on silica gel using chloroform with increasing proportions of ethyl acetate as the eluent. The fractions containing the product are combined and concentrated in vacuo to give the desired compound.

EXAMPLE 8

6-beta-Bromopenicillanic Acid 1-(Ethoxycarbonyloxy)ethyl Ester 1,1-Dioxide

6,6-dibromopenicillanic acid 1-(ethoxycarbonyloxy)ethyl ester 1,1-dioxide

Under a nitrogen atmosphere, 240 mg. of lithium hydroxide was added to 3.91 g. of 6,6-dibromopenicillanic acid sulfone in 30 ml. of diemthylsulfoxide, and the resulting solution allowed to stir at room temperature for 2 hrs. Subsequently, 810 mg. of tetrabutylammonium bromide, 0.56 ml. of N-methylmorpholine and 3.64 g. of alpha-chlorodiethyl carbonate were added to the reaction mixture in the indicated order, and the reaction mixture allowed to stir at room temperature overnight.

The reaction mixture was poured into 50 ml. of 0.1 N hydrochloric acid and washed with diethyl ether. Removal of the ether gave 2.98 g. of the crude product as a brown oil. A 500 mg. sample was chromatographed on silica gel using ethyl acetate-hexane (1:2, vol:vol) as the eluent to give a sample, 210 mg., of the pure product.

6-beta-bromopenicillanic acid 1-(ethoxycarbonyloxy)ethyl ester 1,1-dioxide

To a solution of 2.53 g. of 6,6-dibromopenicillanic acid 1-(ethoxycarbonyloxy)ethyl ester 1,1-dioxide in 125 ml. of dry toluene cooled to −5° C. is added 1.82 g. of diphenylbenzyltin hydride followed by 10 mg. of azobisisobutyronitrile. The resulting solution is irradiated with ultraviolet light for 20 min. with external cooling to maintain the temperature at 25° C. The solvent is removed in vacuo and the residue dissolved in a 1:1 mixture of ethyl acetate-water and the pH adjusted to 6.8. The ethyl acetate is separated and the aqueous further extracted with fresh ethyl acetate. The organic phase and the washings are combined, washed with water and a saturated brine solution and dried over sodium sulfate. Removal of the solvent under reduced pressure gives the desired product.

EXAMPLE 9

Starting with an appropriate 6,6-disubstituted penicillanic ester 1,1-dioxide, and employing the procedure of Example 8, the following compounds are prepared:

6-beta-chloropenicillanic acid crotonolactonyl ester 1,1-dioxide; 6-beta-chloropenicillanic acid ethoxycarbonyloxymethyl ester 1,1-dioxide; 6-beta-bromopenicillanic acid 1-methyl-1-(propoxycarbonyloxy)ethyl ester 1,1-dioxide; 6-beta-bromopenicillanic acid gamma-butyrolacton-4-yl ester 1,1-dioxide; 6-beta-iodopenicillanic acid 4-crotonolactonyl ester 1,1-dioxide; 6-beta-iodopenicillanic acid 1-(butoxycarbonyloxy)ethyl ester 1,1-dioxide.

EXAMPLE 10

6-beta-Bromopenicillanic Acid 1,1-Dioxide Sodium Salt 6-bromo-6-iodopenicillanic acid To 10 ml. of 2.5 N sulfuric acid, 6.21 g. of iodine-bromide and 2.76 g. of sodium nitrite in 75 ml. of methylene chloride cooled to 0° to −5° C. was added 4.32 g. of 6-beta-aminopenicillanic acid over a period of 15 min. After 20 min. stirring at −5° C., 100 ml. of 10% sodium bisulfite was added, care being taken to keep the temperature of the reaction mixture below 10° C. The layers were separated and the aqueous extracted with methylene chloride (3×50 ml.). The combined organic layer and extracts were washed with a saturated brine solution, dried over magnesium sulfate and concentrated in vacuo to give 5.78 g. of the desired intermediate, m.p. 145°–147° C.

6-bromo-6-iodopenicillanic acid 1,1-dioxide

To 4.05 g. of 6-bromo-6-iodopenicillanic acid in 30 ml. of methylene chloride and over-laid with 60 ml. of water was added sufficient 3 N sodium hydroxide to give a pH of 7.0. The aqueous layer was separated, cooled to 5° C. and treated dropwise over a 15 min. period with 1.93 g. of potassium permanganate and 1 ml. of 85% phosphoric acid in 30 ml. of water. The pH was maintained at 5.8–6.2 by the addition of 3 N sodium hydroxide and the temperature was kept at about 5° C. On completion of the addition, 100 ml. of ethyl acetate was added and the pH lowered to 1.5 with 6 N hydrochloric acid. A 10% sodium bisulfite solution (30 ml.) was added until the reaction mixture turned a pale yellow. The organic layer was separated and the aqueous extracted with ethyl acetate (4×50 ml.). The organic layer and extracts were combined, washed with a saturated brine solution, dried over magnesium sulfate and concentrated under reduced pressure to give 3.6 g., m.p. 151°–153° C.

6-β-bromopenicillanic acid 1,1-dioxide sodium salt

To a solution of 3.36 g. of 6-bromo-6-iodopenicillanic acid 1,1-dioxide in 130 ml. of toluene at 5° C. is added, under a nitrogen atmosphere, 1.09 ml. of triethylamine followed by 1.3 g. of dimethyl-t-butylsilyl chloride. Stirring is maintained for 5 min. at 5° C., 60 min. at 25° C. and 30 min. at 45° C., and then the reaction mixture is cooled to 25° C. The triethylamine hydrochloride is removed by filtration and 15 mg. of azobisisobutyronitrile and 2.04 ml. of dibenzylphenyltin hydride is added to the filtrate. The mixture is irradiated with ultraviolet light for 15 min., with external cooling to keep the temperature at about 20°–25° C. The solvent is removed in vacuo and residual material dissolved in a 1:1 mixture of tetrahydrofuran-water. The pH is adjusted to 7.0 and the tetrahydrofuran removed under reduced pressure. The aqueous is treated with 100 ml. of ethyl acetate and the pH adjusted to 1.8 with 6 N hydrochloric acid. The organic layer is separated and the aqueous further extracted with ethyl acetate. The organic layer and extracts are combined, backwashed with a saturated brine solution and dried over sodium sulfate. The organic solution is then treated with 2.2 g. of sodium 2-ethylhexanoate in ethyl acetate and allowed to stir for 1 hour. The resulting precipitated salt is filtered and dried.

PREPARATION A

6-Chloro-6-iodopenicillanic Acid

To 3.38 g of iodine monochloride in 30 ml of dichloromethane was added, with stirring, at 0°–5° C., 11.1 ml of 2.5 N sulfuric acid, followed by 1.92 g of sodium nitrite. At this point, 3.00 g of 6-aminopenicillanic acid was added all at once, and stirring was continued for 30 minutes at 0°–5° C. To the reaction mixture was then added 22.8 ml of 1 M sodium sulfite solution in portions, and the layers were separated. The aqueous layer was washed with further dichloromethane, and then all the organic phases were washed with saturated sodium chloride. The dichloromethane solution was dried (Na$_2$SO$_4$) and evaporated in vacuo giving 3.48 g of the title compound.

The above product was dissolved in 30 ml of tetrahydrofuran, and then 30 ml of water were added. The pH was adjusted to 6.8 with dilute sodium hydroxide and the tetrahydrofuran was removed in vacuo. The remaining aqueous phase was freeze-dried and the residue was washed with diethyl ether. This afforded 3.67 g of the title compound as its sodium salt.

PREPARATION B

6-beta-Chloropenicillanic Acid

A 2.95-g sample of sodium 6-chloro-6-iodopenicillanic acid was converted to the free acid, and then it was dissolved in 125 ml of benzene under nitrogen. To the solution was added 1.08 ml of triethylamine, and the mixture was cooled to 0°–5° C. To the cooled mixture was then added 0.977 ml of trimethylsilyl chloride, and the reaction mixture was stirred at 0°–5° C. for 5 minutes, at 25° C. for 60 minutes and at 50° C. for 30 minutes. The reaction mixture was cooled to 25° C. and the triethylamine hydrochloride was removed by filtration. To the filtrate was added 15 mg of azobisisobutyronitrile, followed by 2.02 ml of tri-n-butyltin hydride. The mixture was then irradiated with ultraviolet light for 15 minutes with cooling to maintain at temperature of ca. 20° C. The solvent was then removed by evaporation in vacuo, and the residue was dissolved in a 1:1 mixture of tetrahydrofuran-water. The pH was adjusted to 7.0 and the tetrahydrofuran was removed by evaporation in vacuo. The aqueous phase was washed with ether, and then an equal volume of ethyl acetate was added. The pH was adjusted to 1.8 and the ethyl acetate layer was removed. The aqueous phase was extracted with further ethyl acetate, and then the combined ethyl acetate solutions were dried and evaporated in vacuo. This afforded 980 mg of 6-beta-chloropenicillanic acid.

The above product was dissolved in tetrahydrofuran, and an equal volume of water was added. The pH was adjusted to 6.8, and the tetrahydrofuran was removed by evaporation in vacuo. The aqueous phase remaining was freeze-dried to give 850 mg of sodium 6-beta-chloropenicillanate. The NMR spectrum ($D_2O$) showed absorption at 5.70 (d, 1H, J=4 Hz), 5.50 (d, 1H, J=4 Hz), 4.36 (s, 1H), 1.60 (s, 3H) and 1.53 (s, 3H) ppm.

PREPARATION C

6-beta-Bromopenicillanic Acid

A mixture of 5.0 g of 6,6-dibromopenicillanic acid, 1.54 ml of triethylamine and 100 ml of benzene was stirred under nitrogen until a solution was obtained. The solution was cooled to 0°–5° C., and 1.78 ml of trimethylsilyl chloride was added. The reaction mixture was stirred at 0°–5° C. for 2–3 minutes, and then at 50° C. for 35 minutes. The cooled reaction mixture was filtered and the filtrate was cooled to 0°–5° C. A small quantity of azobisisobutyronitrile was added followed by 3.68 ml of tri-n-butyltin hydride. The reaction flask was irradiated with ultraviolet light for 15 minutes, and then the reaction was stirred at ca. 25° C. for 1.75 hours. The reaction mixture was irradiated again for 15 minutes and then stirring was continued 2.5 hours. At this point a further small quantity of azobisisobutyronitrile was added, followed by 0.6 ml of tri-n-butyltin hydride (0.6 ml), added and the mixture was again irradiated for 30 minutes. The solvent was then removed by evaporation in vacuo, and to the residue was added 5% sodium bicarbonate solution and diethyl ether. The two-phase system was shaken vigorously for 10 minutes and then the pH was adjusted to 2.0. The ether layer was removed, dried and evaporated in vacuo to give 2.33 g of an oil. The oil was converted into a sodium salt by adding water containing 1 equivalent of sodium bicarbonate followed by freeze drying the solution thus obtained. The afforded sodium 6-beta-bromopenicillanate, contaminated with a small amount of the alpha-isomer.

The sodium salt was purified by chromotography on Sephadex LH-20, combined with some further material of the same quality and re-chromatographed. The NMR spectrum ($D_2O$) of the product thus obtained showed absorptions at 5.56 (s, 2H), 4.25 (s, 1H), 1.60 (s, 3H) and 1.50 (s, 3H) ppm.

PREPARATION D

6-beta-Iodopenicillanic Acid

The title compound is prepared by reduction of 6,6-diiodopenicillanic acid, with tri-n-butyltin hydride, according to the procedure of Preparation B.

PREPARATION E

Pivaloyloxymethyl 6-beta-Bromopenicillanate

To a solution of 280 mg of 6-beta-bromopenicillanic acid in 2 ml of N,N-dimethylformamide is added 260 mg of diisopropylethylamine followed by 155 mg of chloromethyl pivalate and 15 mg of sodium iodide. The reaction mixture is stirred at room temperature for 24 hours, and then it is diluted with ethyl acetate and water. The pH is adjusted to 7.5, and then the ethyl acetate layer is separated and washed three times with water and once with saturated sodium chloride solution. The ethyl acetate solution is then dried using anhydrous sodium sulfate, and evaporated in vacuo to give the title compound.

PREPARATION F

Reaction of the appropriate 6-halopenicillanic acid with 3-phthalidyl chloride, 4-crotonolactonyl chloride, gamma-butyrolacton-4-yl chloride or the requisite alkanoyloxymethyl chloride, 1-(alkanoyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Preparation E, affords the following compounds:
3-phthalidyl 6-beta-chloropenicillanate,
4-crotonolactonyl 6-beta-chloropenicillanate,
gamma-butyrolacton-4-yl 6-beta-bromopenicillanate,
acetoxymethyl 6-beta-bromopenicillanate,
pivaloyloxymethyl 6-beta-bromopenicillanate,
hexanoyloxymethyl 6-beta-iodopenicillanate,
1-(acetoxy)ethyl 6-beta-iodopenicillanate,
1-(isobutyryloxy)ethyl 6-beta-chloropenicillanate,
1-methyl-1-(acetoxy)ethyl 6-beta-chloropenicillanate,
1-methyl-1-(hexanoyloxy)ethyl 6-beta-bromopenicillanate,
methoxycarbonyloxymethyl 6-beta-bromopenicillanate,
propoxycarbonyloxymethyl 6-beta-bromopenicillanate,
1-(ethoxycarbonyloxy)ethyl 6-beta-bromopenicillanate,
1-butoxycarbonyloxy)ethyl 6-beta-iodopenicillanate,
1-methyl-1-(methoxycarbonyloxy)ethyl 6-beta-iodopenicillanate, and
1-methyl-1-(isopropoxycarbonyloxy)ethyl 6-beta-chloropenicillanate,
respectively.

PREPARATION G

6,6-Diiodopenicillanic Acid

A mixture of 15.23 g of iodine, 10 ml of 2.5 N sulfuric acid, 2.76 g of sodium nitrite and 75 ml of dichloromethane was stirred at 5° C., and 4.32 g of 6-aminopenicillanic acid were added over a period of 15 minutes. Stirring was continued at 5°–10° C. for 45 minutes after the addition was complete, and then 100 ml of 10% sodium bisulfite was added dropwise. The layers were separated, and the aqueous layer was further extracted with dichloromethane. The combined dichloromethane layers were washed with brine, dried ($MgSO_4$) and evaporated in vacuo. This afforded 1.4 g of the title compound, contaminated with some 6-iodopenicillanic acid. The product had a melting point of 58°–64° C. The NMR spectrum ($CDCl_3$) showed absorptions at 5.77 (s, 1H), 4.60 (s, 1H), 1.71 (s, 3H) and 1.54 (s, 3H) ppm.

PREPARATION H

Sodium 6-beta-Bromopenicillanate

To a stirred solution of 1.83 g of 6,6-dibromopenicillanic acid and 0.7 ml of triethylamine in 4.6 ml of toluene was added 0.64 ml of trimethylsilyl chloride, at 20° C., under nitrogen. Stirring was continued at 20° C. for 30 minutes, and then the precipitate was removed by filtration. To the filtrate was added, dropwise, under nitrogen, at 20° C., 1.3 ml of triphenyltin hydride in 1 ml of toluene, during 10 minutes. Stirring was continued at 20° C. for 5 hours, and then the reaction mixture was filtered, and stirring was continued a further 1 hour at 20° C. At this point 100 ml of sodium bicarbonate solution was added and the aqueous phase was removed. Ethyl acetate was added to the aqueous phase and the biphasic mixture was cooled to 0°–5° C. The pH was lowered to 1.5 with 6 N hydrochloric acid and the ethyl acetate layer was removed. The latter solution was dried with magnesium sulfate and then 4.2 ml (1.24 mmol/ml) of sodium 2-ethylhexanoate in ethyl acetate was added. The resulting mixture was stored at ca. 5° C. overnight and then it was concentrated to 5 ml volume. The solid was recovered by filtration and washed with acetone to give 380 mg of the title compound, contaminated with about 13% of penicillanic acid sodium salt.

PREPARATION I

Sodium 6-beta-Iodopenicillanate

To a stirred solution of 4.0 g of 6,6-diiodopenicillanic acid in 16 ml of toluene and 10 ml of tetrahydrofuran, under nitrogen was added 1.24 ml of triethylamine followed by 1.146 ml of trimethylsilyl chloride. Stirring was continued for 30 minutes and the precipitate was removed by filtration. To the filtrate was added a solution of 2.09 ml of tri-n-butyltin hydride in 3.1 ml of toluene. After 30 minutes of stirring, 22.38 ml of water was added, and the layers were separated. The organic layer was washed with saturated sodium chloride solution, dried using magnesium sulfate, and then it was concentrated to about two-thirds volume. To this solution was then added a solution containing 8.77 mmole of sodium 2-ethylhexanoate in 7 ml of toluene, at 0° to 5° C., with stirring. Stirring was continued for 1.5 hours at 0° to 5° C. The precipitate which had formed was removed by filtration, and slurried in hexane. The solid was recovered by filtration to give 0.921 g of product, which was a 1:1 mixture of the title compound and its 6-alpha isomer. The two components can be separated by chromatography on sephadex or silica gel.

PREPARATION J

6-Beta-Iodopenicillanic Acid Pivaloyloxymethyl Ester

A. 6,6-diiodopenicillanic acid pivaloyloxy methyl ester

A mixture of 5.94 g. of sodium nitrite in 260 ml. of water and 2.63 g. of 6-beta-aminopenicillanic acid pivaloyloxymethyl ester in 260 ml. of methylene chloride was stirred with cooling in an ice bath. p-Toluenesulfonic acid (1.2 g.) was added in three portions over a period of 30 minutes and the mixture was allowed to stir for one hour at room temperature. The organic phase was separated and dried over sodium sulfate. Iodine (1.3 g.) was added to the organic phase and the resulting solution allowed to stir at room temperature for 4 hours. The solution was washed with aqueous sodium thiosulfate, separated and concentrated in vacuo to a low volume. The residue was chromatographed on silica gel using petroleum ether (b.p. 60°–80°) containing an increasing proportion of ethyl acetate as the eluent. The fractions containing the product were combined, dried over sodium sulfate and concentrated under vacuum to dryness to give 1.43 g., m.p. 136°–138° C. The NMR spectrum (CDCl$_3$) showed absorption at 5.79 (bs, 2H), 5.71 (s, 1H), 4.52 (s, 1H), 1.65 (s, 3H), 1.44 (s, 3H) and 1.21 (s, 9H) ppm.

B. 6-beta-iodopenicillanic acid pivaloyloxymethyl ester

To a solution of 1.29 g. of 6,6-diiodopenicillanic acid pivaloyloxymethyl ester in 8 ml. of benzene under a nitrogen atmosphere was added 500 mg. of triphenyltin hydride and a few crystals (10 mg.) of azobisisobutyronitrile, and resulting reaction mixture was warmed to 50° C. for one hour. An additional 500 mg. of hydride and 10 mg. of nitrile were added and the heating continued with stirring for 3 hours. Column chromatographing on silica gel using petroleum ether (b.p. 60°–80° C.) with an increasing proportion of methylene chloride as the eluent gave 140 mg. of the desired product, m.p. 73°–77° C. The NMR spectrum (CDCl$_3$) showed absorption at 5.9 (d, AB, J=5.8 Hz), 5.82 (d, AB, J=5.8 Hz), 5.66 (d, 1H, AB, J=4.1 Hz), 5.42 (d, 1H, AB, J=4.1 Hz), 4.59 (s, 1H), 1.71 (s, 3H), 1.50 (s, 3H) and 1.24 (s, 9H) ppm.

PREPARATION K

6-Beta-Iodopenicillanic Acid

A. 6,6-diiodopenicillanic acid benzhydryl ester

To a solution of 5.94 g. of sodium nitrite in 250 ml. of water at 5° C. was added with stirring 2.9 g. of 6-beta-aminopenicillanic acid benzhydryl ester tosylate salt in 250 ml. of methylene chloride. p-Toluene sulfonic acid (1.2 g.) was added in three portions over a period of 30 minutes and the mixture allowed to stir for one hour at room temperature. The organic phase was separated, dried over sodium sulfate and treated with 1.3 g. of iodine. The resulting solution was stirred at room temperature for 4 hours and was then washed with an aqueous sodium thiosulfate solution and concentrated to a low volume. The residue was chromatographed on silica gel using petroleum ether with increasing proportions of ethyl acetate as the eluent. The fraction containing the product were combined and concentrated in vacuo to give the desired product.

B. 6-beta-iodopenicillanic acid benzhydryl ester

To a solution of 1.92 g. of 6,6-diiodopenicillanic acid benzhydryl ester in 8 ml. of benzene was added 500 mg. of triphenyltin hydride and 10 mg. of azobisisobutyronitrile, and the resulting reaction mixture allowed to stir under a nitrogen atmosphere at 50° C. for one hour. An additional amount of hydride (500 mg.) and nitrile (10 mg.) was added and heating at 50° C. continued for 3 hours. The solvent was removed under vacuum and the residue chromatographed over silica gel using petroleum ether with increasing proportions of ethyl acetate as the eluent. The fractions containing the product were combined and concentrated to dryness. The NMR spectrum (CDCl$_3$) showed absorption at 7.50 (bs, 10H), 6.97 (s, 1H), 5.66 (d, 1H, AB, J=4.0 Hz), 5.44 (d, 1H, AB, J=4.0 Hz), 4.67 (s, 1H), 1.70 (s, 3H) and 1.40 (s, 3H) ppm.

C. 6-beta-iodopenicillanic acid

Trifluoroacetic acid (0.5 ml.) was added to 80 mg. of 6-beta-iodopenicillanic acid benzhydryl ester in 1 ml. of methylene chloride and the reaction mixture stirred for 30 minutes at room temperature. The mixture was evaporated to dryness to yield 76 mg. of crude product. Purification is effected by chromatography on silica gel.

PREPARATION L

6-Beta-Iodopenicillanic Acid

A. 6,6-diiodopenicillanic acid 4-methoxybenzyl ester

The title compound was prepared from 6-beta-aminopenicillanic acid 4-methoxybenzyl ester following the procedure of Preparation K (Part A).

B. 6-beta-iodopenicillanic acid 4-methoxybenzyl ester

The title compound was prepared from 6,6-diiodopenicillanic acid 4-methoxybenzyl ester using the procedure of Preparation K (Part B). The NMR (CDCl₃) spectrum shows absorption at 7.36 (d, 2H, AA', XX', J=9 Hz), 6.95 (d, 2H, AA', XX', J=9.0 Hz), 5.65 (d, 1H, AB, J=4.2 Hz), 5.42 (d, 1H, AB, J=4.2 Hz), 4.58 (s, 1H), 3.89 (s, 3H), 1.71 (s, 3H), 1.70 (s, 3H) and 1.39 (s, 3H) ppm.

C. 6-beta-iodopenicillanic acid

6-Beta-iodopenicillanic acid 4-methoxybenzyl ester (90 mg.) was dissolved in 2 ml. of methylene chloride to which was then added 1 ml. of trifluoroacetic acid and 3 drops of anisole. The mixture was stirred at room temperature for 5 hours and was then evaporated to dryness. The residue was chromatographed on silica using petroleum ether and then ethyl acetate as the eluent. The fractions containing the product were combined and concentrated to give 40 mg. of the desired product. The NMR (CDCl₃) spectrum showed absorption ca. 9 (bs, 1H), 5.65 (d, 1H, AB, J4.0 Hz), 5.39 (d, 1H, AB, J=4.0 Hz), 4.57 (s, 2H), 1.74 (s, 3H) and 1.57 (s, 3H).

PREPARATION M

Preparation of Benzhydryl 6-alpha-Trifluoromethanesulfonyloxypenicillanate

Sodium nitrite (55 g, 0.80 mole) was added to a cold stirred solution of p-toluenesulfonic acid monohydrate (12.5 g, 0.065 moles) in a mixture of water (1.25 l) and methylene chloride (1.25 l) and the mixture was stirred at 5° C. for 15 minutes. Benzhydryl 6-beta-aminopenicillanate p-toluenesulfonate salt (27.75 g, 0.05 mole) was added and the mixture stirred vigorously at 5°-7° C. for 30 minutes. The organic layer was separated, dried over anhydrous magnesium sulfate and filtered. Powdered magnesium silicate (8 g) was added and the filtrate cooled to 5° C. and stirred while trifluoromethanesulfonic acid (8.0 g, 0.055 mole) was added dropwise over 15 minutes keeping the temperature below 10° C. The addition was accompanied by vigorous evolution of nitrogen. After stirring for a further 15 minutes the solution was filtered and the filtrate was evaporated to dryness under vacuum at 40° C. to yield the product as a tan foam (22 g, 92%).

N.M.R. (CD₃COCD₃) delta: 1.35 (s, 3H), 1.60 (s, 3H), 4.82 (s, 1H), 5.72 (d, 1H, J=1.5 Hz), 5.90 (s, 1H), 6.95 (s, 1H), 7.3 (m, 10H).

T.L.C. (silica/ethyl acetate): Rf 0.8: A small sample was recrystallized from hexane and had m.p. 44°-45° C. (dec).

PREPARATION N 6-alpha-Trifluoromethylsulfonyloxypenicillanic Acid

4-Methoxybenzyl 6-alpha-trifluoromethylsulfonyloxypenicillanate (100 mg.) was dissolved in trifluoroacetic acid (1 ml.) and after 15 seconds evaporated to dryness. Column chromatography of the residue on silica eluting with petrol containing increasing amounts of ethyl acetate yielded 62 mg. impure product, which was triturated with diisopropyl ether and purified by preparative t.l.c. on silica with 5% acetic acid in ethyl acetate to give pure 6-alpha-trifluoromethylsulfonyloxypenicillanic acid (17 mg.).

T.L.C.: Rf 0.45 (5% acetic acid/ethyl acetate on SiO₂).

N.M.R. (CDCl₃) delta: 1.57 (s, 3H); 1.61 (s, 3H); 4.56 (s, 1H); 5.51 (s, 2H); 9.07 (bs, HO group).

I.R. (film): 1815 cm⁻¹ (beta-lactam carbonyl).

PREPARATION O 6-alpha-Trifluoromethylsulfonyloxypenicillanic Acid 4-methoxybenzyl Ester A solution of trifluoromethane sulfonyl chloride (0.70 g.) in chloroform (2 ml.) was added dropwise to a stirred ice-cold solution of 6-alpha-hydroxypenicillanic acid 4-methoxybenzyl ester (0.93 g.) and triethylamine (0.55 g.) in chloroform (50 ml.). After 15 minutes the solution was washed with water (50 ml.), dried (MgSO₄) and evaporated to dryness. The product was chromatographed on silica eluting with pentane containing an increasing proportion of dichloromethane.

Evaporation of the relevant fractions gave 6-alpha-trifluoromethylsulfonyloxypenicillanic acid 4-methoxybenzyl ester (0.70 g.), m.p. 69°-71° C.

Analysis %: Found: C, 43.59; H, 3.81; N, 2.62. C₁₇H₁₈NO₇SF₃ requires: C, 43.50; H, 3.84; N, 2.99.

N.M.R. (CDCl₃) delta: 1.36 (s, 3H); 1.53 (s, 3H); 3.80 (s, 3H); 4.52 (s, 1H); 5.12 (s, 2H); 5.48 (2H); 7.08 (q, 4H).

T.L.C. (silica/dichloromethane): Rf 0.3.

PREPARATION P 6-beta-Iodopenicillanic Acid (A) A mixture of 6-alpha-trifluorosulfonyloxypenicillanic acid 4-methoxybenzyl ester (5 g.), sodium iodide (12.5 g.) and acetone (100 ml.) was stirred at room temperature for 46 hours. The resulting mixture was concentrated to 10 ml., diluted with water (200 ml.) and extracted with ether (200 ml.). The ether extract was dried over MgSO₄ and evaporated to yield 6-beta-iodopenicillanic acid 4-methoxybenzyl ester as an oil (4.8 g.).

(B) Trifluoroacetic acid (2 ml.) was added to a solution of the product from A (0.38 g.) in dichloromethane (20 ml.). The solution was stirred at room temperature for 30 minutes and the solution was then evaporated under vacuum and the residue chromatographed on a column of silica eluting with a 1:3 mixture of ethyl acetate and petroleum ether (b.p. 60°-80° C.). The relevant fractions containing the product were combined and evaporated to a low volume. The crystalline precipitate was collected by filtration, washed with a 1:1 mixture of dichloromethane and pentane and dried to yield 6-beta-iodopenicillanic acid (27 mg.), m.p. 120° C. (dec.)

The product was spectroscopically and chromatographically identical to a reference sample.

N.M.R. (CDCl₃) delta: 1.57 (s, 3H); 1.74 (s, 3H); 4.57 (s, 1H+1H); 5.39 (d, 1H, J=4.0 Hz); 5.65 (d, 1H, J=4.0 Hz); 9.0 (bs, 1H).

PREPARATION Q 6-beta-Iodopenicillanic Acid (A) The procedure of Preparation O, Part A, was followed using 6-alpha-trifluoromethylsulfonyloxypenicillanic acid benzhydryl ester to give 6-beta-iodopenicillanic acid benzhydryl ester.

N.M.R. (CDCl₃) delta: 1.24 (s, 3H); 1.65 (s, 3H); 4.62 (s, 1H); 5.36 (d, 1H); 5.56 (d, 1H); 6.95 (s, 1H); 7.36 (s, 10H).

(B) 6-beta-Iodopenicillanic acid benzhydryl ester (80 mg.) was dissolved in dichloromethane (1 ml.) and trifluoroacetic acid (0.5 ml.) added. The solution was stirred at room temperature for 30 minutes and then evaporated to dryness to yield 76 mg. of product, identified by thin-layer chromatography, i.r. spectrum and n.m.r. to be 6-beta-iodopenicillanic acid contaminated with some benzhydryl-derived by-product.

PREPARATION R

Sodium 6-beta-Iodopenicillanate (A) Bis(trimethylsilyl)acetamide (3.19 g., 157 mmoles) was added to a solution of 6-alpha-trifluoromethylsulfonyloxypenicillanic acid (5 g., 143 mmoles) in acetone (50 ml.) and the solution was stirred at 35°–40° C. for 30 minutes. Sodium iodide (2.35 g., 157 mmoles) was added to the resulting solution of 6-alpha-trifluoromethylsulfonyloxypenicillanic acid trimethylsilyl ester and the mixture was stirred at 60°–65° C. for 30 minutes. The solvent was evaporated under vacuum to yield 6-beta-iodopenicillanic acid trimethylsilyl ester as a thick red oil.

(B) The product from (A) was stirred with ethyl acetate (50 ml.) and water (50 ml.), the organic layer was separated, washed with water (2×25 ml.) and dried over anhydrous magnesium sulfate. A solution of sodium 2-ethylhexanoate (3.57 g., 215 mmoles) was added to the acetone solution of the acid and the mixture stirred at room temperature for 30 minutes.

The crystalline precipitate was collected by filtration, washed with ethyl acetate and ether and dried to yield sodium 6-beta-iodopenicillanate (3.3 g., 66%) identical to a reference sample.

PREPARATION S

6-alpha-Hydroxypenicillanic Acid 4-Methoxybenzyl Ester

Anisyl chloride (50.6 g.) was added to a stirred solution of 6-alpha-hydroxypenicillanic acid (71 g.) in N,N-dimethylformamide (540 ml.) containing triethylamine (57 g.). The mixture was stirred at room temperature for 17 hours and then partitioned between water (1 l.) and ethyl acetate (1 l.). The organic phase was separated, washed in turn with water (2×500 ml.), saturated sodium bicarbonate (500 ml.) and brine (500 ml.) and dried over magnesium sulfate. Evaporation of the solvent gave an oil which was chromatographed on silica eluting with petroleum ether (b.p. 60°–80° C.) to give 6-alpha-hydroxypenicillanic acid 4-methoxybenzyl ester (15 g., 13%) as an oil.

N.M.R. (CDCl$_3$) delta: 1.35 (s, 3H); 1.50 (s, 3H); 3.78 (s, 3H); 4.42 (s, 1H); 4.77 (d, 1H); 5.10 (s, 2H); 5.22 (d, 1H); 7.05 (q, 4H).

PREPARATION T

Starting with the appropriate 6-β-aminopenicillanic acid ester and employing the procedure of Example 10, the following 6-β-iodopenicillanic acid esters are prepared:

6-β-iodopenicillanic acid 3-phthalidyl ester, 6-β-iodopenicillanic acid 1-(acetoxy)ethyl ester; 6-β-iodopenicillanic acid 4-crotonolactonyl ester; 6-β-iodopenicillanic acid γ-butyrolacton-4-yl ester; 6-β-iodopenicillanic acid acetoxymethyl ester; 6-β-iodopenicillanic acid hexanoyloxymethyl ester; 6-β-iodopenicillanic acid 1-(isobutyryloxy)ethyl ester; 6-β-iodopenicillanic acid methoxycarbonyloxymethyl ester; 6-β-iodopenicillanic propoxycarbonyloxymethyl ester; 6-β-iodopenicillanic acid 1-(ethoxycarbonyloxy)ethyl ester; 6-β-iodopenicillanic acid 1-(butoxycarbonyl)ethyl ester; 6-β-iodopenicillanic acid 1-methyl-1-(methoxycarbonyloxy)ethyl ester; and 6-β-iodopenicillanic acid 1-methyl-1-(isopropoxycarbonyl)ethyl ester.

PREPARATION U

6-β-Chloropenicillanic Acid Acetoxymethyl Ester

6-Chloro-6-iodopenicillanic acid acetoxymethyl ester

To a solution of 5.03 g. of 6-chloro-6-iodopenicillanic acid in 50 ml. of acetone and 50 ml. of acetonitrile is added 900 mg. of di-isopropylethylamine followed by 0.7 ml. of acetoxymethyl bromide. The resulting solution is allowed to stir at room temperature for 48 hrs. An additional 0.7 ml. of bromide and 900 mg. of amine are added and the stirring is continued for an additional 48 hrs. The solution is concentrated in vacuo to dryness and the residue suspended in ethyl acetate. The insolubles are filtered and the filtrate washed successively with water, 1 N hydrochloric acid and saturated aqueous sodium bicarbonate solution. The organic phase is dried, and the solvent removed in vacuo. The residual product is chromatographed on silica gel using methylene chloride as the eluent. The fractions containing the desired material are combined and the solvent removed under vacuum.

6-β-Chloropenicillanic acid acetoxymethyl ester

A solution of 833 mg. of 6-chloro-6-iodopenicillanic acid acetoxymethyl ester and 700 mg. of diphenylmethyltin hydride in 20 ml. of toluene is warmed to 80° C. under a nitrogen atmosphere for 4.5 hrs. The solvent is removed in vacuo, and the residue chromatographed on silica gel using methylene chloride as the eluate. Fractions containing the product are combined and concentrated to dryness to give 6-β-chloropenicillanic acid acetoxymethyl ester.

PREPARATION V

Employing the procedures of Preparation U, and starting with the requisite halide, the following 6-β-chloropenicillanic acid esters are prepared:

6-β-chloropenicillanic acid 3-phthalidyl ester; 6-β-chloropenicillanic acid 1-methyl-1-(isopropoxy)ethyl ester; 6-β-chloropenicillanic acid pivaloyloxymethyl ester; 6-β-chloropenicillanic acid 4-crotonolactonyl ester; 6-β-chloropenicillanic acid 1-methyl-1-(methoxycarbonyloxy)ethyl ester; 6-β-chloropenicillanic acid γ-butyrolactonyl-4-yl ester; 6-β-chloropenicillanic acid hexanoyloxymethyl ester; 6-β-chloropenicillanic acid 1-(butoxycarbonyloxy)ethyl ester; 6-β-chloropenicillanic 1-(isobutyryloxy)ethyl ester 6-β-chloropenicillanic acid methoxycarbonyloxymethyl ester; and 6-β-chloropenicillanic acid propoxycarbonyloxymethyl ester.

PREPARATION W

6-β-Bromopenicillanic Acid

To 4000 ml. of dry toluene was added 1000 g. of 6,6-dibromopenicillanic acid and 390 ml. of triethylamine and the resulting slurry slowly cooled to 20°–25° C. Trimethylchlorosilane (355 ml.) was added dropwise over a 10 min. period and the reaction mixture was allowed to warm to 25° C. The triethylamine hydrochloride was filtered and the solids washed with 1.75 l. of toluene. To the combined original filtrate and washings in a flask under a nitrogen atmosphere was added 733 ml. of tri-n-butyltin hydride in 1000 ml. of toluene at the rate of 18–20 ml./min. When the addition was complete, the reaction mixture was allowed to stir for one hour, and was then quenched in 7 l. of a saturated sodium bicarbonate solution. The layers were separated and the organic layer further extracted with an additional 3 l. of the saturated sodium bicarbonate solution. The aqueous layer and extracts were combined, treated with 5 l. of ethyl acetate and treated with sufficient 12 N hydrochloric acid to bring the pH to 1.55. The ethyl acetate layer was separated and the aqueous further extracted with 2.5 l. of ethyl acetate. The original layer and extracts were combined, dried over sodium sulfate and treated with 2.26 l. of an ethyl acetate solution containing an equivalent amount of sodium 2-ethylhexanoate. The precipitate sodium salt was kept at 8°–10° C. overnight and was then filtered and dried to give 391.5 g. of crystalline material.

The above sodium salt (380 g.) was dissolved in 1.9 l. of deionized water at 8° C. and was then treated with sufficient 6 N hydrochloric acid to give a pH of 1.5. After one hour of stirring in the cold (3°–5° C.) the precipitated free acid was filtered and washed with 500 ml. of cold water. To the water-wet free acid in 2 l. of ethyl acetate at 8° C. was added 100 ml. water and the pH adjusted to 1.5 with 6 N hydrochloric acid. The organic layer was separated and the aqueous further extracted with ethyl acetate. The organic layer and the extracts were combined treated with charcoal and dried over magnesium sulfate. To the stirred ethyl acetate is added about one equivalent of sodium 2-ethylhexanoate in 811 ml. of ethyl acetate. After 1.25 hrs. of stirring the precipitated solids were filtered and dried to give 262 g. of sdium 6-β-bromopenicillanate.

To further purify the compound, the above sodium salt was dissolved in 1300 ml. of deionized water and the pH adjusted to 1.3 at 6°–8° C. The precipitated solids were stirred for 1.5 hrs. at 6°–8° C. and were filtered and washed with 300 ml. water. The free acid was treated with 2 l. of ethyl acetate and 200 ml. of water, and the pH adjusted with 6 N hydrochloric acid to 1.35–1.40. The organic layer was separated and dried over magnesium sulfate. To the filtrate was added 802 ml. of ethyl acetate containing about an equivalent of sodium 2-ethylhexanoate. The precipitated sodium salt was allowed to stir for one hour at room temperature and was filtered and dried to give 227 g. of the desired crystalline sodium salt.

A 40.0 g. sample of the above sodium salt was added to 200 ml. of water and the resulting solution at ice-bath temperature was treated with 6 N hydrochloric acid to pH 1.6. The precipitated free acid was filtered, reslurried twice in water. Drying in vacuo at room temperature overnight gave 34.05 g. of the desired crystalline compound, m.p. 190°–195° C. (dec.).

Anal. Calc'd for $C_8H_{10}NO_3SBr$: C, 34.3; H, 3.6; N, 5.0. Found: C, 34.4; H, 3.7; N, 5.0.
$[\alpha]_D = +292°$.

PREPARATION X

6-β-Bromopenicillanic Acid Acetoxymethyl Ester 6,6-dibromopenicillanic acid acetoxymethyl ester To a solution of 5 g. of 6,6-dibromopenicillanic acid and 900 mg. of di-isopropylethylamine in 50 ml. of acetone and 50 ml. of acetonitrile was added 0.7 ml. of acetoxymethyl bromide, and the resulting solution allowed to stir at room temperature for 48 hrs. An additional 0.7 ml. of the bromide and 900 mg. of amine were then added and the stirring continued for a further 48 hrs. The solvent was removed in vacuo and the residue treated with ethyl acetate and filtered. The filtrate was washed with water, 1 N hydrochloric acid and saturated aqueous sodium bicarbonate, and was then dried over sodium sulfate. The residue which remained after the solvent was removed under vacuum was chromatographed on silica gel using methylene chloride as the eluent. The fractions containing the desired material were combined and concentrated to give a colorless oil which solidified on standing. Recrystallization of a portion gave the analytical sample, m.p. 79°–82° C. The NMR spectrum (CDCl$_3$) showed absorption at 5.78 (s, 3H), 4.51 (s, 1H), 2.10 (s, 3H), 1.61 (s, 3H) and 1.48 (s, 3H) ppm.

6-β-bromopenicillanic acid acetoxymethyl ester

A mixture of 430 mg. of 6,6-dibromopenicillanic acid acetoxymethyl ester and 350 mg. of triphenyltin hydride was heated under a nitrogen atmosphere to 90° C. for 5 hrs. The residue was chromatographed on 120 g. of silica gel using methylene chloride as the eluent. Fractions containing the product were combined and concentrated in vacuo to give the desired product. The NMR spectrum (CDCl$_3$) showed absorption at 5.81 (s, 2H) 5.65 (s, 2H), 4.51 (s, 1H), 2.05 (s, 3H), 1.65 (s, 3H) and 1.48 (s, 3H) ppm.

PREPARATION Y

6-β-Bromopenicillanic Acid Pivaloyloxymethyl Ester 6,6-dibromopenicillanic acid pivaloyloxymethyl ester To a solution of 1.8 ml. of pivaloyloxymethyl chloride and 5 g. of 6,6-dibromopenicillanic acid in 15 ml. of dimethylformamide at 0° C. was added 1.9 ml. of triethylamine and the resulting reaction mixture allowed to stir at room temperature for 16 hrs. The reaction mixture was poured into 150 ml. of water and 150 ml. of ethyl acetate and the pH adjusted to 2.0 with 6 N hydrochloric acid. The organic phase was washed with water, aqueous sodium bicarbonate solution and a saturated brine solution, and then dried over magnesium sulfate. Removal of the solvent in vacuo gave 4.7 g. of a red solid which was purified by column chromatography, m.p. 98°–99° C. The NMR spectrum (CDCl$_3$) showed absorption at 5.80 (s, 2H), 5.75 (s, 1H), 4.5 (s, 1H), 1.61 (s, 3H), 1.47 (s, 3H) and 1.21 (s, 9H) ppm.

6-β-bromopenicillanic acid pivaloyloxymethyl ester

The reduction procedure employed in Preparation X was used on 6,6-dibromopenicillanic acid pivaloyloxymethyl ester to give the desired product. The NMR of the product showed absorption at 5.85 (d, 1H, J=5 Hz), 5.76 (d, 1H, J=5 Hz), 5.56 (d, 1H, J=4 Hz), 5.31 (d, 1H, J=4 Hz), 4.53 (s, 1H), 1.67 (s, 3H), 1.49 (s, 3H) and 1.22 (s, 9H) ppm.

PREPARATION Z

Starting with 6,6-dibromopenicillanic acid and the appropriate halide, and employing the procedure of Preparation X, the following compounds are prepared.

1-(acetoxy)ethyl 6-beta-bromopenicillanate,
isobutyryloxymethyl 6-beta-bromopenicillanate,
n-butyryloxymethyl 6-beta-bromopenicillanate,
1-(n-butyryloxy)ethyl 6-beta-bromopenicillanate,
1-methyl-1-(acetoxy)ethyl 6-beta-bromopenicillanate,
1-methyl-1-(pivaloyloxy)ethyl 6-beta-bromopenicillanate,
4-crotonolactonyl 6-beta-bromopenicillanate, gamma-butyrolacton-4-yl 6-beta-bromopenicillanate,
3-phthalidyl 6-beta-bromopenicillanate,
methoxycarbonyloxymethyl 6-beta-bromopenicillanate,
isobutyloxycarbonyloxymethyl 6-beta-bromopenicillanate,
1-(ethoxycarbonyloxy)ethyl 6-beta-bromopenicillanate and
1-methyl-1-(propoxycarbonyloxy)ethyl 6-beta-bromopenicillanate.

I claim:

1. (2S,5R,6R)-6-beta-Bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof.

2. A compound in accordance with claim 1, (2S,5R,6R)-6-beta-bromo-3,3-dimethyl-7-oxo-4-thia-1-azabicyclo[3.2.0]heptane-2-carboxylic acid, S,S-dioxide.

3. A penicillanic acid derivative of the formula

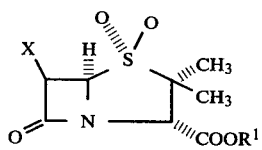

and the pharmaceutically-acceptable base salts thereof, wherein $R^1$ is hydrogen or an ester-forming residue readily hydrolyzable in vivo, said ester-forming residue readily hydrolyzable in vivo being selected from the group consisting of alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl;

and X is chloro, bromo or iodo.

4. A compound according to claim 3, wherein X is bromo.

5. The compound according to claim 4, wherein $R^1$ is hydrogen.

6. A compound according to claim 4, wherein $R^1$ is said alkanoyloxymethyl.

7. The compound according to claim 4, wherein $R^1$ is pivaloyloxymethyl.

8. A compound according to claim 4, wherein $R^1$ is said 1-(alkoxycarbonyloxy)ethyl.

9. The compound according to claim 4, wherein $R^1$ is 1-(ethoxycarbonyloxy)ethyl.

10. A method of increasing the effectiveness of a beta-lactam antibiotic in a human subject, which comprises co-administering with said beta-lactam antibiotic, to said human subject, a beta-lactam antibiotic effectiveness increasing amount of a penicillanic acid derivative of the formula

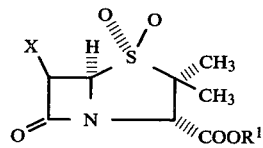

or a pharmaceutically-acceptable base salt thereof;
wherein $R^1$ is hydrogen or as ester-forming residue readily hydrolyzable in vivo, said ester-forming residue readily hydrolyzable in vivo being selected from the group consisting of alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl;

X is chloro, bromo or iodo;

and said beta-lactam antibiotic is selected from the group consisting of:
6-(2-phenylacetamido)penicillanic acid,
6-(2-phenoxyacetamido)penicillanic acid,
6-(D-2-amino-2-phenylacetamido)penicillanic acid,
6-(D-2-amino-2-[4-hydroxyphenyl]acetamido)-penicillanic acid,
6-(2-carboxy-2-phenylacetamido)penicillanic acid
and the pharmaceutically acceptable salts thereof.

11. A pharmaceutical composition which comprises an antibacterially effective amount of a penicillanic acid derivative of the formula

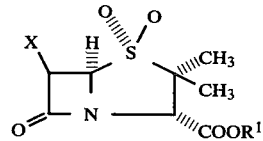

or a pharmaceutically-acceptable base salt thereof, and a pharmaceutically-acceptable carrier;
wherein $R^1$ is hydrogen or an ester-forming residue readily hydrolyzable in vivo, said ester-forming residue readily hydrolyzable in vivo being selected from the group consisting of alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl;

X is chloro, bromo or iodo;

and said pharmaceutically-acceptable carrier is present in an amount in the range from 5 to 80 percent by weight.

* * * * *